United States Patent
de Ana et al.

(10) Patent No.: US 8,226,582 B2
(45) Date of Patent: Jul. 24, 2012

(54) CONTROLLING ACOUSTIC MODES IN TISSUE HEALING APPLICATIONS

(75) Inventors: F. Javier de Ana, Chapel Hill, NC (US); Robin A. Chivers, York (GB); Neill M. Pounder, Cary, NC (US)

(73) Assignee: Smith & Nephew, Inc., Memphis, TN (US)

( * ) Notice: Subject to any disclaimer, the term of this patent is extended or adjusted under 35 U.S.C. 154(b) by 446 days.

(21) Appl. No.: 12/296,333

(22) PCT Filed: Apr. 7, 2007

(86) PCT No.: PCT/US2007/066197
§ 371 (c)(1),
(2), (4) Date: Apr. 27, 2009

(87) PCT Pub. No.: WO2007/118224
PCT Pub. Date: Oct. 18, 2007

(65) Prior Publication Data
US 2009/0306551 A1    Dec. 10, 2009

Related U.S. Application Data

(60) Provisional application No. 60/790,502, filed on Apr. 7, 2006, provisional application No. 60/870,934, filed on Dec. 20, 2006.

(51) Int. Cl.
*A61N 7/00* (2006.01)
(52) U.S. Cl. .......................................................... 601/2
(58) Field of Classification Search .................. 601/2–4; 600/439
See application file for complete search history.

(56) References Cited

U.S. PATENT DOCUMENTS

| 5,411,024 A | * | 5/1995 | Thomas et al. | ............... 600/325 |
| 5,904,659 A | * | 5/1999 | Duarte et al. | ..................... 601/2 |
| 7,628,764 B2 | | 12/2009 | Duarte et al. | |
| 2002/0016557 A1 | | 2/2002 | Duarte et al. | |

FOREIGN PATENT DOCUMENTS

| WO | WO 9002512 A | * | 3/1990 |
| WO | WO9807470 A1 | | 2/1998 |
| WO | WO03013654 A1 | | 2/2003 |
| WO | WO2004093994 A1 | | 11/2004 |

OTHER PUBLICATIONS

International Search Report for International Application No. PCT/US2007/066197, mailed Sep. 21, 2007, 4 pages.
International Preliminary Report on Patentability for International Application No. PCT/US2007/066197, mailed Oct. 8, 2008, 6 pages.
Examiner's First Report for corresponding Australian Application No. 2007234743, mailed Jul. 29, 2010, 2 pages.

(Continued)

*Primary Examiner* — Ruth S Smith
(74) *Attorney, Agent, or Firm* — Fish & Richardson P.C.

(57) ABSTRACT

A modal converter assembly [10] for healing tissue, the modal converter assembly [10] comprises a transducer [5] and a body [8]. The transducer [5] is configured to transmit acoustic waves into the tissue from a tissue surface. The body [8] is configured to house the transducer [5] above the tissue surface such that the acoustic waves transmitted into the tissue are transmitted at an oblique angle relative to the tissue surface. The acoustic waves are transferred as shear waves and longitudinal waves to treat a damaged portion of the tissue.

12 Claims, 8 Drawing Sheets

OTHER PUBLICATIONS

First Office Action for corresponding Chinese Application No. 200780021310, mailed Oct. 8, 2010, 7 pages.

Examination Report (pursuant to Article 94(3) EPC)) for corresponding European Application No. 07760294.4, mailed Sep. 15, 2010, 3 pages.

Translation of Office Action issued in Chinese Application No. 2007/80021310.X, mailed Aug. 5, 2011, 1 page.

Translation of Office Action issued in Japanese Application No. 2009-504500, mailed Sep. 20, 2011, 4 pages.

* cited by examiner

CONTROLLING ACOUSTIC MODES IN TISSUE HEALING APPLICATIONS

CROSS-REFERENCE TO RELATED APPLICATIONS

This application is a U.S. National Phase filing of International Application No. PCT/US2007/066197 which claims priority to U.S. Provisional Patent Application 60/790,502 filed Apr. 7, 2006, titled "Controlling Acoustic Modes in Tissue Healing Applications" and U.S. Provisional Patent Application 60/870,934 filed Dec. 20, 2006, titled "Angle Dependence of Low Intensity Pulsed Ultrasound Transmission in Bone." The applications are herein incorporated by reference.

BACKGROUND OF THE INVENTION

1. Field of the Invention

The present invention relates to therapeutic ultrasound devices for treating a human body and, more particularly, to controlling the angles at which the acoustic waves are delivered from a transducer to the human body.

2. Related Art

Ultrasound has been used as a therapeutic technique in physical medicine for over 45 years. It has been a recommended treatment technique for adjunctive therapy for the treatment of pain, soft tissue injury, and joint dysfunction including osteoarthritis, periarthritis, bursitis, tenosynovitis, and a variety of musculoskeletal syndromes. Additionally, ultrasound has been used in applications such as acceleration of wound healing, phonophoresis of topical drugs, treatment of scar tissue, and treatment of sports injuries.

The therapeutic biological effects of ultrasound may be characterized into two major areas: thermal and nonthermal. The nonthermal effects can include acoustic streaming, cavitation, and other mechanical effects over the broad range of ultrasonic frequencies from about 0.05 MHz (megahertz) to about 5.0 MHz. The electrical output from a signal generator is converted into mechanical vibration through a transducer which is generally made of a piezoelectric material such as lead zirconate titanate (PZT), single-crystal ferroelectric relaxors such as PMN-PZ-PT, or the like. The mechanical vibration produces an acoustic wave which travels through the tissue and is absorbed in the propagating process. The rate of viscous absorption and the associated increase in temperature are dependent on the micro-structural properties of the tissue-type encountered, the frequency of the acoustic wave, the spatial-temporal acoustic intensity and the degree of non-linear propagation in tissue. The acoustic energy may be in the form of a continuous wave or a pulsed wave, depending on the therapeutic application, and is typically transferred from the transducer to the patient's tissue using an acoustic coupling material, such as an ultrasonic gel, lotion, hydrogel, or water. Acoustic intensities of 0.03 to 3.0 W/cm2 (Watts per square centimeter) are typically applied for therapeutic purposes, in pulsed or continuous modes, allowing treatment of bone fractures and acute, as well as chronic, tissue injury.

Typically, therapeutic ultrasound treatment is administered by utilizing a piezoelectric transducer normal to the skin tissue interface to generate acoustic longitudinal waves that propagate in tissue, primarily as longitudinal waves, to the treatment area. If the incident longitudinal waves are not normal to the piezoelectric transducer/skin tissue interface, the resulting refracted acoustic waves in the subsequent soft tissue propagate as quasi-longitudinal waves and quasi-shear waves at various refraction angles. As a result, it is often difficult to administer the acoustic waves to patients in the desired alignment with the targeted tissue area using the means for therapeutic ultrasound devices that are currently available.

International Publication No. WO 03/013654A1 taught that shear and longitudinal waves could be controlled and delivered to a tissue by means of a modal converter in the form of a trapezoidal shaped cross-section of a low viscous loss material. The modal converter is a large block of rubber that needs ultrasound coupling gel between the tissue surface area and the rubber block. The shape and design of such a block is difficult to position and restrain on a patient to allow consistent delivery of ultrasound. In addition, the placement of the transducer and the rubber block in relation to the injury requires the center of the block to be offset from the fracture, which is counter-intuitive for most people applying the device to a fracture. The acoustic requirements for this rubber block are such that the material is highly attenuating and requires a much higher incident intensity to be delivered to the first face of the block and has a substantial drain on the battery life of the device and thus on its usability.

Although International Publication No. WO 03/013654A1 explains how to maximize longitudinal and shear waves along the surface of the bone to accelerate periosteal healing, it does not consider the importance of shear waves for the other processes involved in tissue repair. Periosteal direct bone formation is one of the key processes involved in fracture repair, but bone and tissue healing is not limited to only that process. If it is important to provide longitudinal and shear waves to aid specific types of tissue healing, then it would also be important to identify critical angles that result in the desired type of tissue healing.

There remains a need in the art for improved methods and systems for delivering ultrasonic waves to damaged tissue. Further, there remains a need in the art for methods and systems that use ultrasonic waves applied at critical angles to achieve specific types of tissue healing.

SUMMARY OF THE INVENTION

An aspect of the invention provides a modal converter assembly for healing tissue. The modal converter assembly comprises a transducer and a body. The transducer is configured to transmit acoustic waves into the tissue from a tissue surface. The body is configured to house the transducer above the tissue surface such that the acoustic waves transmitted into the tissue are transmitted at an oblique angle relative to the tissue surface. The acoustic waves are transferred as shear waves and longitudinal waves to treat a damaged portion of the tissue.

An embodiment of the invention provides a modal converter assembly wherein the transducer is a piezoelectric element.

Another embodiment of the invention further comprises a modal converter being made of a material having a speed of sound similar to the speed of sound of the soft tissue. The modal converter is placed within the body and between the transducer and the soft tissue such that the angle between the transducer and the tissue surface is an oblique angle.

Another embodiment of the invention further comprises a spring configured to bias the transducer toward the tissue surface.

Yet another embodiment of the invention further comprises a cap configured to attach to the body. The spring has a first end and a second end. The first end is attached to the cap and the second end is attached to the transducer.

Another embodiment of the invention provides a modal converter assembly wherein the transducer comprises a plurality of acoustic wave generating elements. The plurality of acoustic wave generating elements are oriented along the tissue surface.

Another embodiment of the invention further comprises a signal generator. The signal generator is configured to control the acoustic waves generated in the transducer.

Another embodiment of the invention provides a modal converter assembly wherein acoustic waves are temporally shifted such that the sum of the acoustic waves transmitted into the tissue are transmitted at an oblique angle relative to the tissue surface.

Another embodiment of the invention provides a modal converter assembly wherein the oblique angle is in the range from about 18 to 71 degrees from normal.

Another aspect of the invention provides a modal converter assembly for healing tissue. The modal converter assembly comprises a transducer, a body, and a modal converter. The transducer is configured to transmit acoustic waves into the tissue from a tissue surface. The body is configured to house the transducer above the tissue surface. The modal converter is made of a material having a speed of sound similar to the speed of sound of the soft tissue. The modal converter is placed within the body and between the transducer and the soft tissue such that the angle between the transducer and the tissue surface is an oblique angle. The acoustic waves are transferred as shear waves and longitudinal waves to treat a damaged portion of the tissue.

Another aspect of the invention provides a modal converter assembly for healing tissue. The modal converter assembly comprises a transducer and a body. The transducer includes a plurality of acoustic wave generating elements configured to transmit acoustic waves into the tissue from a tissue surface. The plurality of acoustic wave generating elements are oriented along the tissue surface. The body is configured to house the transducer above the tissue surface such that the acoustic waves transmitted into the tissue are transmitted at an oblique angle relative to the tissue surface. The acoustic waves are transferred as shear waves and longitudinal waves to treat a damaged portion of the tissue.

Yet another aspect of the invention provides a modal converter assembly for healing tissue. The modal converter assembly comprises a transducer and a body. The transducer is configured to transmit acoustic waves into the tissue from a tissue surface. The body is configured to house the transducer above the tissue surface such that the acoustic waves transmitted into the tissue are transmitted at an oblique angle relative to the tissue surface. The acoustic waves are temporally shifted such that the sum of the acoustic waves transmitted into the tissue are transmitted at an oblique angle relative to the tissue surface. The acoustic waves are transferred as shear waves and longitudinal waves to treat a damaged portion of the tissue.

Yet another aspect of the invention provides a method for treating tissue. The method orients a transducer over a tissue surface. The method rotates the transducer relative to the tissue surface. The method also transmits an acoustic wave into the tissue. The acoustic waves are transmitted at an oblique angle relative to the tissue surface. The acoustic waves are transferred as shear waves and longitudinal waves to treat a damaged portion of the tissue.

An advantage of the invention provides healing of tissue by implementing acoustical waves at an oblique angle to the tissue surface. At oblique angles, shear waves or a combination of shear waves and longitudinal waves may treat a damaged portion of the tissue.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
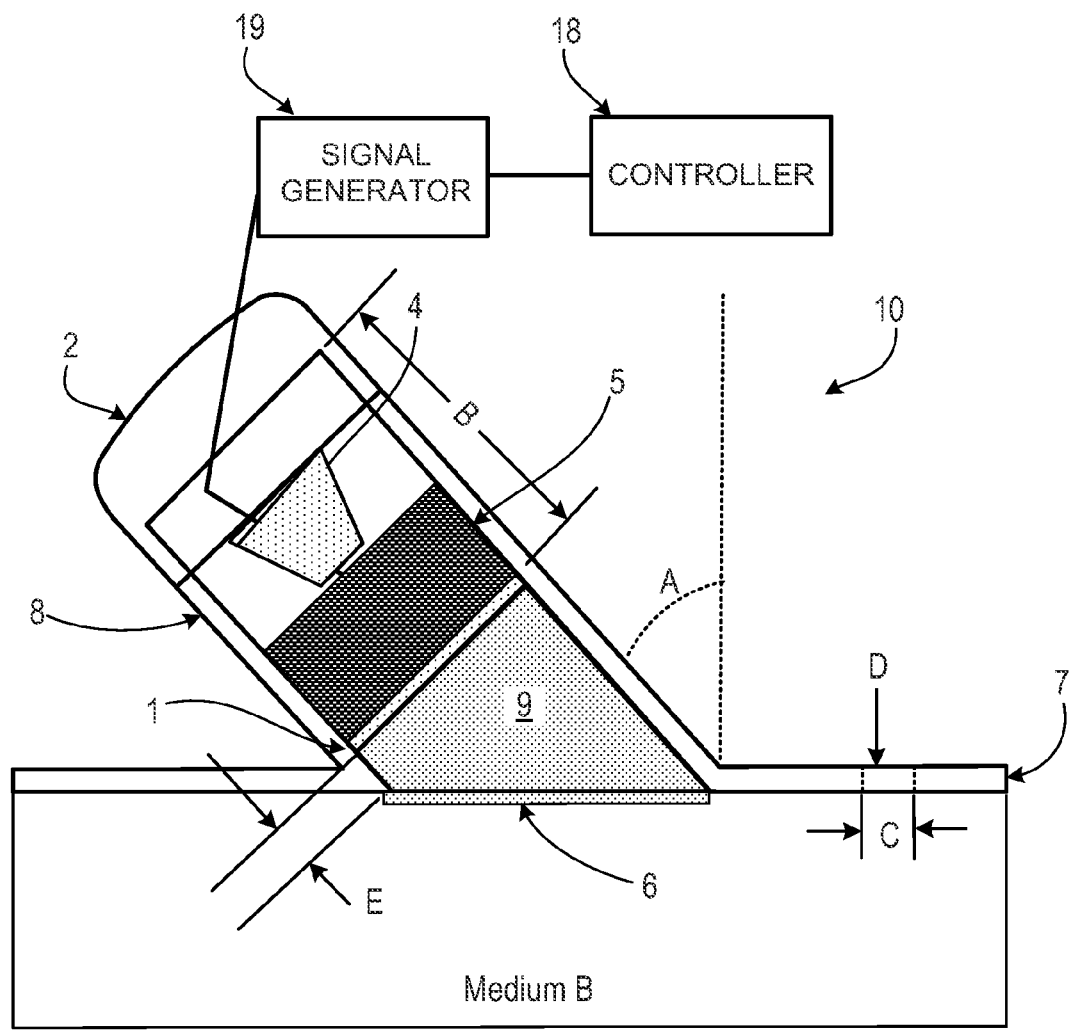
FIG. 1 is a cross-sectional side view of a first embodiment of a modal converter assembly.
Figure 2:
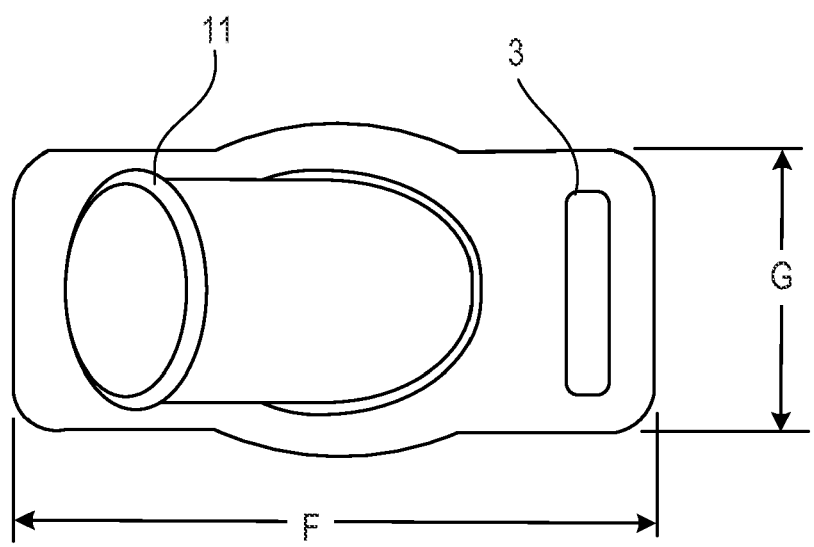
FIG. 2 is a top view of a body of the modal converter assembly.
Figure 3:
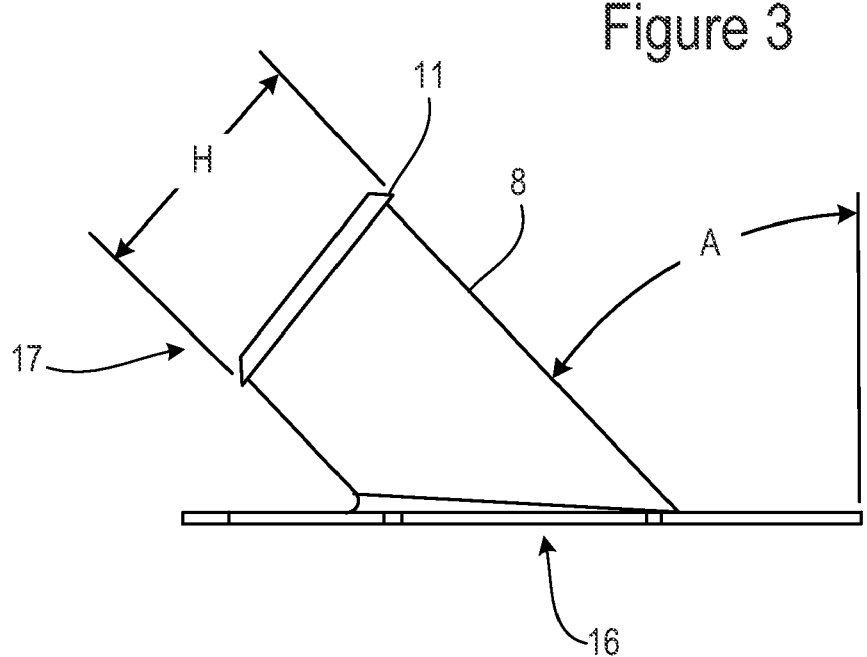
FIG. 3 is a side view of the body shown in FIG. 2.
Figure 4:
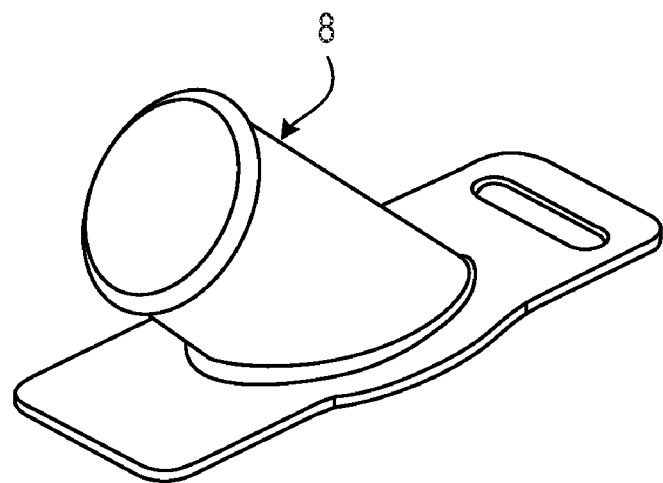
FIG. 4 is a perspective view of the body shown in FIG. 2.
Figure 5:
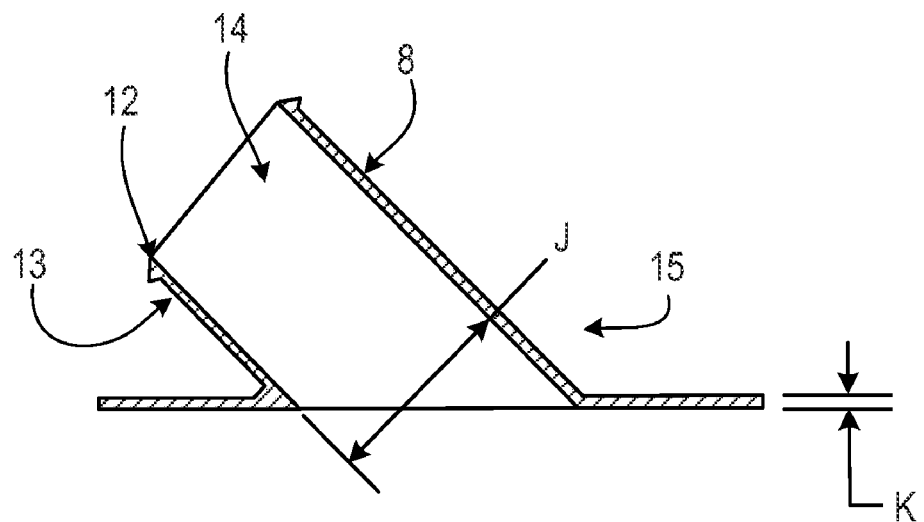
FIG. 5 is a cross-sectional side view of the body shown in FIG. 2.

The following description of the preferred embodiment(s) is merely exemplary in nature and is in no way intended to limit the invention, its application, or uses.

FIGS. 1-5 illustrate a modal converter assembly 10 to deliver ultrasound waves into a medium B which may be composed of soft tissue and/or bone. The ultrasound waves promote healing of a wound in the soft issue and/or healing of a fracture in the bone. The modal converter assembly 10 includes a cap 2, a spring 4, a transducer 5, a base 7, a body 8, and a modal converter 9. The cap 2, base 7, and body 8 form a housing structure to house the transducer 5, spring 4, and modal converter 9. The transducer 5 is electrically coupled to a signal generator 19 and controller 18 to control wave propagation through the modal converter 9 and the medium B.

In the depicted embodiments, the base 7 is shown assuming that the interface with the medium B is flat. However, those skilled in the art would understand that the base 7 can be shaped to fit the interface with medium B at a position above medium B where the generation of shear waves is controlled. For example, the base 7 may be curved to fit over an arm or a leg of a patient, or may be irregularly shaped to fit over irregular surfaces.

In some embodiments, the base 7 includes an aperture 3, such as a hole or slot. The aperture 3 may be used to store the modal converter assembly 10 or to attach the base 7 to the medium B. In addition, the aperture may be used as a locator for positioning the modal converter assembly 10 over the medium B. The base 7, in the embodiments of FIGS. 1-5, has dimensions F, G, and K. Dimension F is about 102 millimeters, dimension G is about 38 millimeters, and dimension K is about 1.5 millimeters. Such an embodiment may be easily wielded and manageable over the majority of body surfaces, other dimensions may be used for body surfaces that may require smaller or larger dimensions of the modal converter assembly 10. The body 8 is shaped to receive the transducer 5.

The transducer 5 is constructed of materials and designs that are commonly used in ultrasound applications. The transducer 5 may have piezoelectric properties and may be made from, as examples, a ceramic material, a single-crystal relaxor ferroelectric, lead zirconate titanate, lead metaniobate, barium titanate, and piezoelectric co-polymers of polyvinylidene fluoride (PVDF). Alternatively, the transducer 5 may have magnetostrictive properties. The transducer 5 generates an ultrasound wave to be transmitted into the medium B via the modal converter 9. The ultrasound waves are generated from a driving signal received in the transducer through the signal generator 19. The spring 4 biases the transducer 5 against the modal converter 9 so that the ultrasound waves travel from the transducer 5 through the modal converter 9 and into the medium B.

In the embodiment depicted in FIGS. 1-5, the body 8 is a cylindrical, hollow tube, as the transducer 5 has a circular cross-section, but other shapes may be used. The body 8 has an inner portion 14 and an outer portion 15. In the embodiments depicted in FIGS. 1-5, the body 8 has an inner wall 12 and an outer wall 13 which define the inner portion 14 and the outer portion 15, respectively. The inner wall 12 of the body 8 is dimensioned such that the transducer 5 fits tightly within the body 8. The inner wall 12 may have a diameter the same as or slightly larger than the diameter of the transducer 5. For example, the diameter of the inner wall 12 may be about 0 to about 2 mm larger than the diameter of the transducer 5. The body 8 also has a proximal end 16 and a distal end 17. The cap 2 is connected to the body 8 at the distal end 17. For example, the body 8 may have a lip 11 such that the cap 2 snaps onto the body 8. Further, the spring 4 is mounted between the cap 2 and the transducer 5 in order to exert pressure and positively bias the transducer 5. In some embodiments, the spring 4 may be mounted to the cap 2. The spring 4 biases the transducer 5 toward the proximal end 16 of the body 8. The body 8 is mounted at an oblique angle A relative to the base 7. The body 8 has dimensions H and J. In the embodiment depicted in FIGS. 1-5, dimension H is about 33 millimeters and dimension J is about 31 millimeters but other dimensions may be used.

The modal converter 9 may be composed of suitable low attenuation materials which include, but are not limited to, thermoplastics, thermosets, elastomers and mixtures thereof. Useful thermoplastics include, but are not limited to, ethyl vinyl acetate, available from USI Corp (c/o Plastic Systems, Marlboro, Mass.), ecothane CPC 41, available from Emerson and Cumming (Deway and Almay Chemical division, Canton, Mass.), and polyurethane RP 6400, available from Ren Plastics (a Division of Ciba Geigy, Fountain Valley, Calif.). Useful thermosets include, but are not limited to, epoxies such as Spurr epoxy, available from Ernest F. Fullam, Inc. (Schenectady, N.Y.) and Stycast, available from Emerson and Cumming. Other thermosets may include polymerized esters of acrylic acid, such as n-octyl ester of acrylic acid, n-nonyl ester of acrylic acid, or 2-ethyl pentyl acrylate. Useful elastomers include, but are not limited to, RTV 60 and RTV 90, which are available from General Electric (Silicon Products Division, Waterford, N.Y.). Other elastomers may include natural rubber, synthetic rubber, such as oil-filled and peroxide-cured cis-butadiene rubber, or gel pad material, such as polyglycerol hydrogel.

The modal converter 9 is fitted between the transducer 5 and the medium B. The modal converter 9 may have a low ultrasound attenuation and speed of sound similar to that of soft tissue. The bottom surface of the modal converter 9 that is in contact with the medium B is at an oblique angle relative to the body 8. The dimension E of the modal converter 9 is such that the spring 4 exerts at least some pressure on the transducer 5. Two thin layers of coupling material, such as hydrogel, mineral oil, or water, are applied to ensure that the maximum ultrasound power gets transmitted into the tissue from the transducer 5. A first layer 1 is applied between the transducer 5 and the modal converter 9. A second layer 6 is applied between the modal converter 9 and the medium B.

The modal converter 9 is acoustically coupled to the transducer 5 with the first layer 1 having an acoustic impedance comparable to the acoustic impedance of the modal converter 9, preferably an acoustic impedance within plus or minus ten percent of the acoustic impedance of the modal converter 9. In some embodiments, the acoustic impedance of the modal converter 9 is almost equal to that of human soft tissue. Additionally, the modal converter 9 is composed of materials preferably having a longitudinal velocity that is less than the longitudinal velocity for human musculo-skeletal soft tissue and that is less than the longitudinal velocity for bone tissue.

The acoustic waves which emanate from the transducer 5 are controlled spatially and temporally by the system controller 18. The design and fabrication of the system controller 18 are well known to those who practice the art. The system controller 18 is electrically connected to the signal generator 19, and the signal generator 19 is electrically connected to the transducer 5. The system controller 18 triggers the programmable signal generator 19 to produce ultrasonic excitation signals that are sent to the transducer 5. The transducer 5 receives the excitation signal and emits an acoustic longitudinal wave that propagates through the modal converter material 9 and on to medium B.

The transducer 5 produces specific sequential or simultaneous transmissions of acoustic waves, controlled by the system controller 18, in order to noninvasively irradiate or interrogate the medium B ultrasonically. The system controller 18 may be a programmable microprocessor, but may also include, though is not limited to, integrated circuits, analog devices, programmable logic devices, personal computers or servers. The timing sequences may be established by the user at any time or established during the manufacturing process.

The modal converter assembly 10 may be used to administer therapeutic treatment composed of an ultrasound dosage administered once or twice a day, and repeated daily for several months to effectively stimulate the healing process. In some embodiments, one dosage of acoustic waves ranges between 1 and 60 minutes in length for the transducer 5. The modal converter assembly 10 may be used to facilitate and enhance application of therapeutic ultrasound dosages to shallow or deep anatomical structures, or both, in an effort to expedite tissue wound healing, including both the endosteal and periosteal healing phases in the bone fracture healing process.

Figure 6:
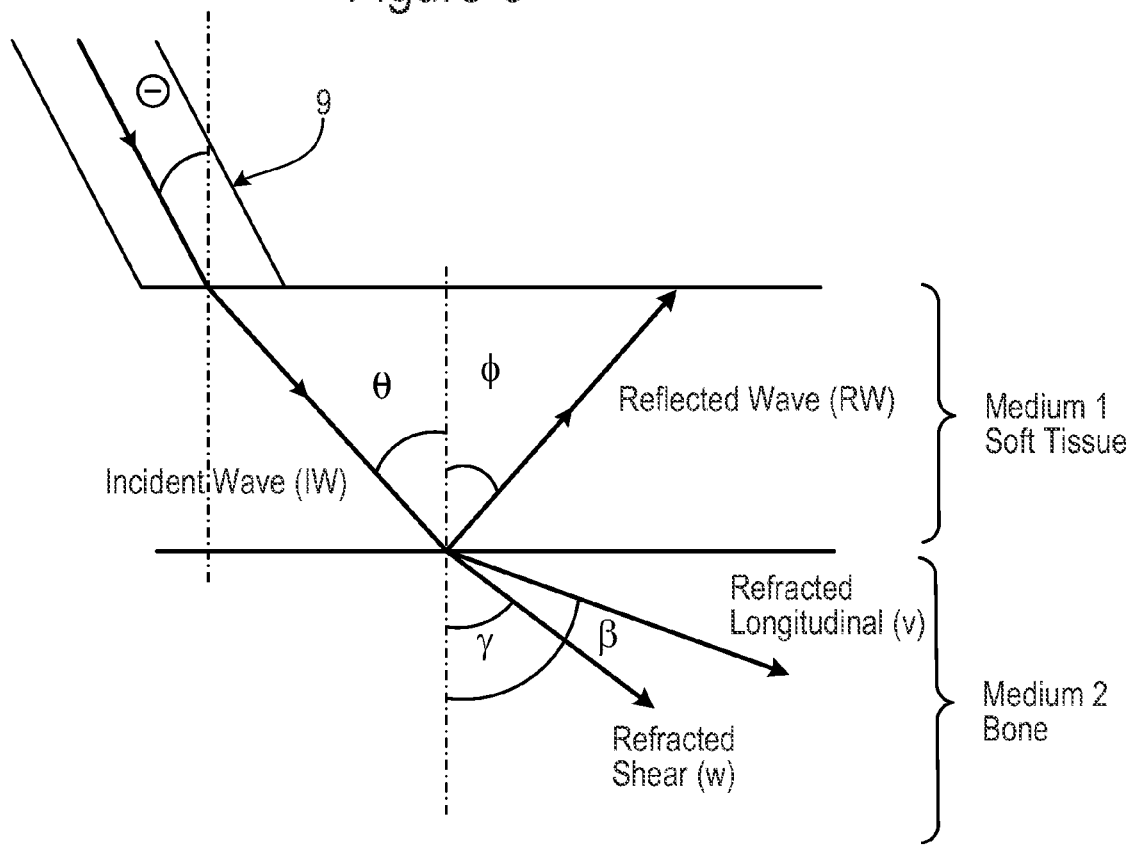
FIG. 6 is a graph illustrating longitudinal and shear waves.

FIG. 6 graphically illustrates incident waves IW onto an interface between soft tissue and bone and the resulting reflected waves RW, refracted shear waves W, and refracted longitudinal waves V. Ultrasonic waves emanate from the transducer 5 (not shown in FIG. 6), travel through the modal converter 9, which is at an angle $\Theta$ with respect to the normal, and enter into a first medium, such as soft tissue, as the incident wave IW at an angle $\theta$. The incident wave IW continues through the first medium until it reaches a second medium, such as bone. At that point, a portion of the incident wave IW is reflected off the second medium as the reflected wave RW at an angle $\Phi$, a portion is refracted as the refracted shear wave W at an angle $\gamma$, and a portion is refracted as the longitudinal wave V at an angle $\beta$. As it is believed that refracted shear waves W and refracted longitudinal waves V promote different types of healing, it is important to identify critical angles of γ and β that maximize the respective type of wave. By identifying the critical angles and comparing the critical angles to the corresponding angle θ of the incident wave IW, the modal converter 9 can be constructed and arranged to provide predetermined specific types of healing or combinations thereof.

Figure 7:
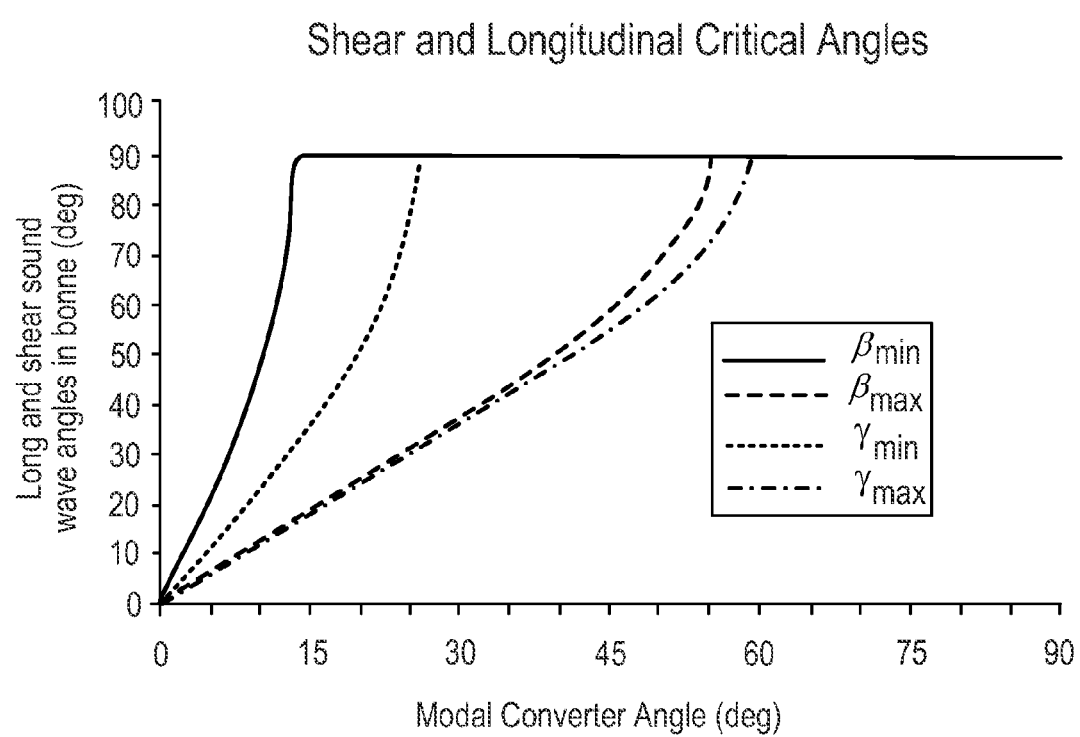
FIG. 7 is a graph comparing longitudinal and shear waves.

FIG. 7 graphically illustrates an exemplary method of determining the modal converter angle Θ for a desired amount of shear waves W (best seen in FIG. 6) and/or longitudinal waves V (best seen in FIG. 6). Four plots are included in the graph showing the angle at which the refracted waves travel in medium 2 (bone) assuming four different combinations of material properties for soft tissue, bone and the modal converter. For example, if only shear waves W parallel to the interface were desired, the modal converter angle Θ would be selected to be about 60 degrees. However, if only shear waves W into the medium were desired, the modal converter angle Θ would be selected to be about 55 degrees. If a combination of shear waves W and longitudinal waves V into the medium are desired, the angle Θ of the modal converter 9 would be selected to be about 35 degrees. However, FIG. 7 is only exemplary as the relevant angles depend largely upon the material of the modal converter, the material of the second medium, and may further depend upon the geometry of the interface between each material. Assuming sound waves travel through the modal converter material at a speed of about 1390 m/sec, longitudinal sound waves travel through the second medium at a speed in the range of about 3000 m/sec to about 3800 m/sec, and shear sound waves travel through the second medium at a speed in the range of about 1630 m/sec to about 1890 m/sec, the actual critical angles have been determined to be from about 22 to about 28 degrees to maximize longitudinal waves V traveling parallel to the interface between the first and second media, from about 48 to about 59 degrees to maximize shear waves W traveling parallel to the interface, and from about 36 to about 41 degrees to maximize the combination of longitudinal waves V traveling parallel to the interface and shear waves W traveling into the second medium. In general, the range of the modal converter angle to achieve longitudinal waves is from about 9 degrees to about 71 degrees, whereas the range of the modal converter angle to achieve shear waves is from about 18 degrees to about 76 degrees.

Figure 8:
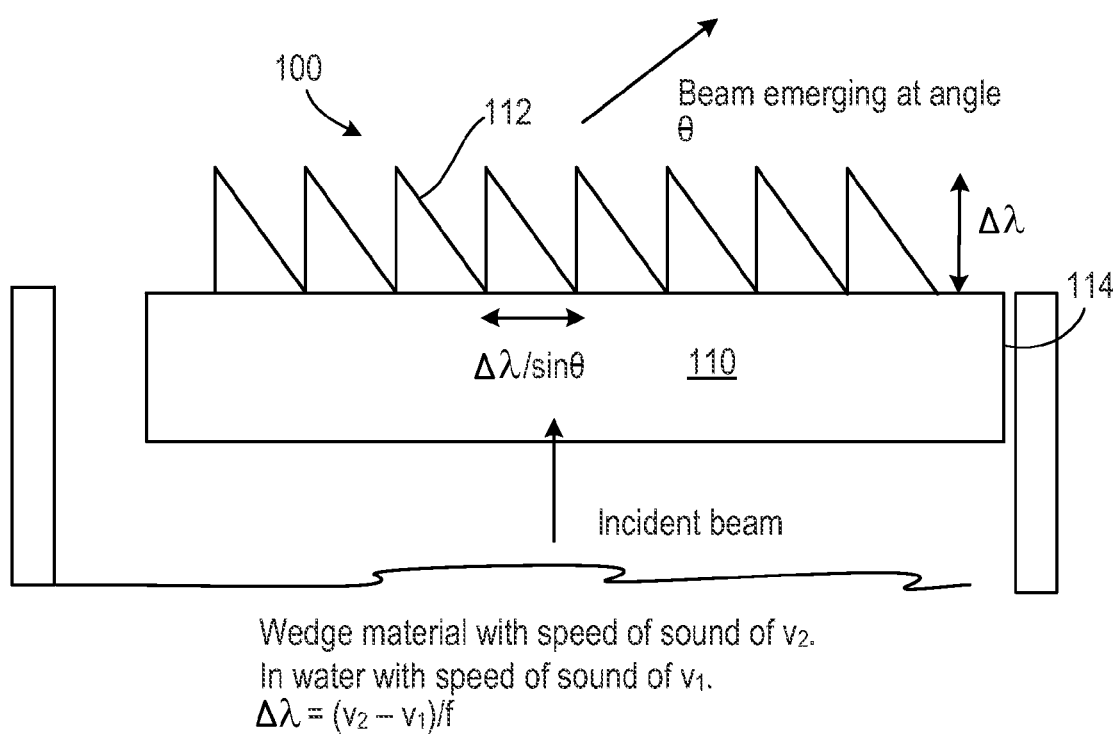
FIG. 8 is a second embodiment of the modal converter assembly.

FIG. 8 illustrates a second embodiment of the modal converter assembly, generally indicated by reference numeral 100. The modal converter assembly 100 includes a transducer 110, a modal converter 112, and a body 114. The transducer 110 and the modal converter 112 are mounted to the body 114. The modal converter 112 provides a grating on the surface of the transducer 110 to direct the ultrasonic waves in a predetermined direction. Selection of the grating pattern and the grating spacing of the modal converter 112 enables the longitudinal waves emitted from the transducer 110 to undergo an angular shift.

Figure 9:
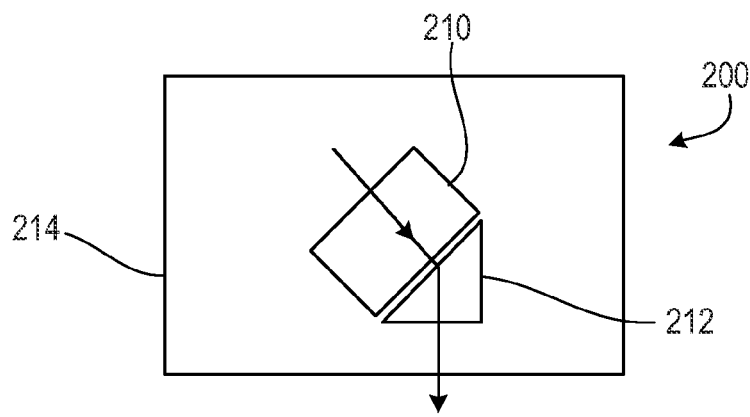
FIG. 9 is a third embodiment of the modal converter assembly.

FIG. 9 illustrates a third embodiment of the modal converter assembly, generally indicated by reference numeral 200. The modal converter assembly 200 includes a piezoelectric element 210, a modal converter 212, and a body 214. The piezoelectric element 210 and the modal converter 212 are mounted within the body 214. The piezoelectric element 210 is mounted at an angle relative the bottom surface of the body 210. The modal converter 212 redirects the waves produced by the piezoelectric element 210.

Figure 10:
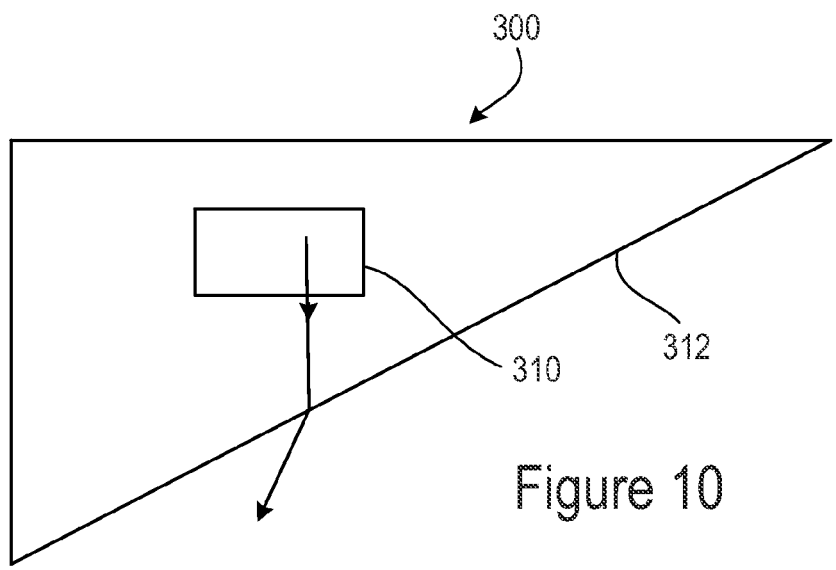
FIG. 10 is a fourth embodiment of the modal converter assembly.

FIG. 10 illustrates a fourth embodiment of the modal converter assembly, generally indicated by reference numeral 300. The modal converter assembly 300 includes a piezoelectric element 310 and a modal converter 312. In this embodiment, the modal converter 312 also functions as a housing or body for the piezoelectric element 310. The piezoelectric element 310 is mounted at an angle relative the bottom surface of the modal converter 312. The modal converter 312 redirects the waves produced by the piezoelectric element 310.

Figure 11:
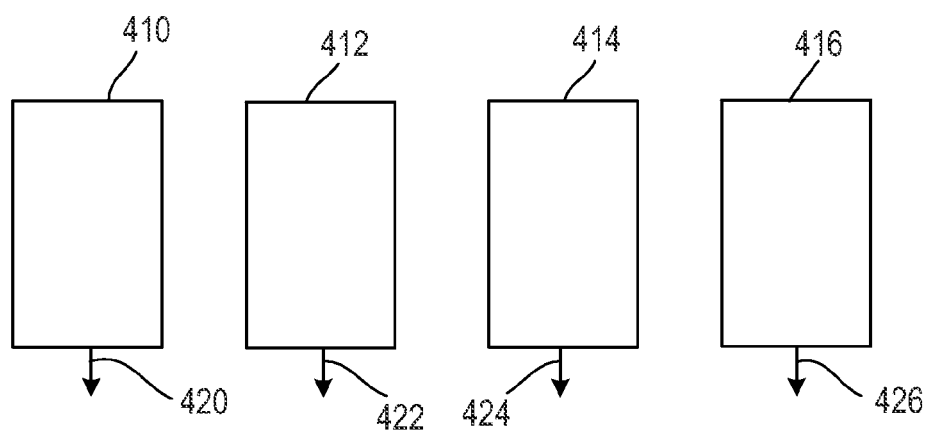
FIG. 11 is a fifth embodiment of the modal converter assembly.

FIG. 11 illustrates a fifth embodiment of the modal converter assembly, generally indicated by reference numeral 400. The modal converter assembly 400 includes a plurality of transducers 410, 412, 414, 416. The transducers 410, 412, 414, 416 produce corresponding waves 420, 422, 424, 426. A system controller, similar to the system controller shown in FIG. 1, can be used to control the engagement of each respective transducer 410, 412, 414, 416. Thus, as an example, the system controller can sequentially engage each transducer 410, 412, 414, 416 to provide gross angular shear or longitudinal waves. By controlling the time delay between sequential operations of the transducers 410, 412, 414, 416, the modal converter assembly 400 can provide waves at a predetermined angle. Thus, the modal converter assembly 400 can control the amount of delivered shear and/or longitudinal waves.

As shown in the embodiments, the piezoelectric may deliver shear waves as a therapy by changing the angle of the piezoelectric transducer relative to the medium either physically or temporally. Materials such as a modal converter may be shaped to adjust the angle of the piezoelectric relative to the medium. Additionally, multiple piezoelectric elements may be used sequentially to achieve a similar effect.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A modal converter assembly for healing tissue, the modal converter assembly comprising:
   a. a transducer configured to transmit acoustic waves;
   b. a body configured to house the transducer, the body including a base and a tubular housing, wherein the tubular housing extends at an oblique angle from the base, and wherein the transducer is located in the tubular housing; and
   c. a modal converter, wherein a material of the modal converter has a speed of sound similar to the speed of sound in the tissue, the modal converter being placed within the tubular housing and having a first end coupled to the transducer and a second end coplanar with at least a portion of the base such that, when the base is coupled to tissue, acoustic waves generated by the transducer are transmitted through the modal converter and into the tissue at the oblique angle relative to a surface of the tissue, wherein the acoustic waves are transferred as shear waves and longitudinal waves to treat a damaged portion of the tissue.

2. The modal converter assembly of claim 1, wherein the transducer is a piezoelectric element.

3. The modal converter assembly of claim 1, further comprising a spring configured to bias the transducer toward the modal converter.

4. The modal converter assembly of claim 3, further comprising a cap attached to the tubular housing, the spring having a first end and a second end, the first end being attached to the cap and the second end being attached to the transducer.

5. The modal converter assembly of claim 4, wherein the tubular housing includes a lip such that the cap engages on to the tubular housing.

6. The modal converter assembly of claim 4, wherein the tubular housing comprises a proximal end and a distal end, wherein the proximal end is proximate the base and the distal end is proximate the cap.

7. The modal converter assembly of claim 6, wherein the spring is attached to the cap such that the spring biases the transducer toward the proximal end of the tubular housing.

8. The modal converter assembly of claim 1, further comprising a signal generator, the signal generator being configured to control the acoustic waves transmitted by the transducer.

9. The modal converter assembly of claim 1, wherein the oblique angle is in a range from about 18 to 71 degrees from normal.

10. The modal converter assembly of claim 1, wherein the material of the modal converter is selected from the group consisting of thermoplastics, thermosets and elastomers.

11. The modal converter assembly of claim 1, wherein the base includes an aperture that is configured for attaching the base to a treatment site.

12. The modal converter assembly of claim 1, wherein the tubular housing includes an inner wall, and a diameter of the inner wall is about 2 mm larger than a diameter of the transducer.

* * * * *